(12) United States Patent
Memo et al.

(10) Patent No.: US 10,183,990 B2
(45) Date of Patent: Jan. 22, 2019

(54) ANTIBODY BINDING A LINEAR EPITOPE OF HUMAN P53 AND DIAGNOSTIC APPLICATIONS THEREOF

(71) Applicant: DIADEM S.R.L., Brescia (BS) (IT)

(72) Inventors: Maurizio Memo, Monticelli Brusati (IT); Daniela Letizia Uberti, Brescia (IT)

(73) Assignee: DIADEM S.R.L, Brescia (IT)

( * ) Notice: Subject to any disclaimer, the term of this patent is extended or adjusted under 35 U.S.C. 154(b) by 0 days.

(21) Appl. No.: 15/515,693

(22) PCT Filed: Sep. 25, 2015

(86) PCT No.: PCT/EP2015/072094
§ 371 (c)(1),
(2) Date: Mar. 30, 2017

(87) PCT Pub. No.: WO2016/050630
PCT Pub. Date: Apr. 7, 2016

(65) Prior Publication Data
US 2018/0057572 A1    Mar. 1, 2018

(30) Foreign Application Priority Data
Sep. 30, 2014  (IT) .............................. TO2014A0776

(51) Int. Cl.
*C07K 16/18*   (2006.01)
*G01N 33/68*   (2006.01)
*C07K 16/32*   (2006.01)

(52) U.S. Cl.
CPC .............. *C07K 16/18* (2013.01); *C07K 16/32* (2013.01); *G01N 33/6896* (2013.01); *C07K 2317/34* (2013.01); *G01N 2333/4748* (2013.01); *G01N 2800/2821* (2013.01); *G01N 2800/56* (2013.01); *G01N 2800/7042* (2013.01)

(58) Field of Classification Search
None
See application file for complete search history.

(56) References Cited

FOREIGN PATENT DOCUMENTS

| WO | 94/12202 A1 | 6/1994 |
| WO | 00/32175 A2 | 6/2000 |
| WO | 2008/147186 A1 | 12/2008 |
| WO | WO2010037395 | * 4/2010 |

OTHER PUBLICATIONS

Caneveli "Cognitive frailty: what is still missing" J Nutr Health Ageing 19(3):273-5 (abstract only) (Year: 2015).*
Kelaiditi "Cognitive frailty: rational and definition from an iana/iagg international consensus group" j nutr health ageing 17(9):726-34 (abstract only) (Year: 2013).*
Chen "Enhancement and destruction of antibody function by somatic mutation: unequal occurrence is controlled by V gene combinatorial associations" EMBO Journal vol. 14 No. 1 2 pp. 2784-2794 (Year: 1995).*
Kussie "A Single Engineered Amino Acid Substitution Changes Antibody Fine Specificity" J immunol 152(1):146-52 (Year: 1994).*
International Search Report, dated Dec. 16, 2015 (4 pages).
B. Vojtesek et al., "Conformational changes in p53 analyzed using new antibodies to the core DNA binding domain of the protein", Oncogene, Nature Publishing Group, vol. 10, No. 2, Jan. 19, 1995, pp. 389-393, cited in the ISR.
L. Buizza et al., "Conformational Altered p53 as an Early Marker of Oxidative Stress in ALzheimer's Disease", PLOS ONE, vol. 7, Issue 1, Jan. 5, 2012, p. e29789, cited in the ISR (11 pages).
D. Uberti et al., "Identification of a mutant-like conformation of p53 in fibroblasts from sporadic Alzheimer's disease patients", Neurobiology of Aging, vol. 27, No. 9, Sep. 1, 2006, pp. 1193-1201, cited in the ISR.
T. Fujiwara et al., "A compound CP-31398 suppresses excitotoxicity-induced neurodegeneration", Biochemical and Biophysical Research Communications, vol. 440, No. 3, Aug. 26, 2013, pp. 359-363, cited in the ISR.
M. Memo et al., "A conformational specific anti p53 monoclonal antibody able to recognize population at risk to develop Alzheimer's disease", BioVaria, Munich 2015, Jun. 1, 2015, cited in the ISR (3 pages).
L. Buizza et al., "Conformational altered p53 affects neuronal function: relevance for the response to toxic insult and growth-associated protein 43 expression", Cell Death and Disease, vol. 4, No. 2, Feb. 1, 2013, p. e484, cited in the ISR (10 pages).
T. R. Hupp, "Regulation of p53 protein rough alterations in protein-folding pathways", CMLS Cellular and Molecular Life Sciences, vol. 55, No. 1, Jan. 1, 1999, pp. 88-95, cited in the ISR.
M. K. Danks et al., "Differences in epitope accessibility of p53 monoclonal antibodies suggest at least three conformations or states of protein binding of p53 protein in human tumor cell lines", Cell Death and Differentiation, vol. 5, No. 8, Aug. 1, 1998, pp. 678-686, cited in the ISR.

* cited by examiner

Primary Examiner — Adam Weidner
(74) Attorney, Agent, or Firm — Jacobson Holman, PLLC.

(57) ABSTRACT

The invention relates to an anti-human p53 antibody suitable for specifically binding a linear epitope which is exposed only in a conformationally altered isoform of the characteristic p53 protein of patients with Alzheimer's disease or prone to develop Alzheimer's disease or cognitive impairment during ageing. Methods and diagnostic and prognostic kits are also described.

2 Claims, 5 Drawing Sheets

Specification includes a Sequence Listing.

FIG.1

MEEPQSDPSV EPPLSQETFS DLWKLLPENN VLSPLPSQAM
DDLMLSPDDI EQWFTEDPGP DEAPRMPEAA PPVAPAPAAP TPAAPA-
PAPS WPLSSSVPSQ KTYQGSYGFR LGFLHSGTAK SVTCTYSPAL
NKMFCQLAKT CPVQLWVDST PPPGTRVRAA IYKQSQHMTE
VVRRCPHHER CSDSDGLAPP QHLIRVEGNL RVEYLDDRNT
FRHSVVVPYE PPEVGSDCTT IHYNYMCNSS CMGGMNRRPI LTIIT-
LEDSS GNLLGRNSFE VRVCACPGRD RRTEEENLRK KGEPHHELPP
GSTKRALPNN TSSSPQPKKK PLDGEYFTLQ IRGRERFEMF RELNEA-
LELK DAQAGKEPGG SRAHSSHLKS KKGQSTSRHK KLMFKTEGPD SD cont vs SAD * p<0,01
cont vs FAD # p<0,05

FIG.3
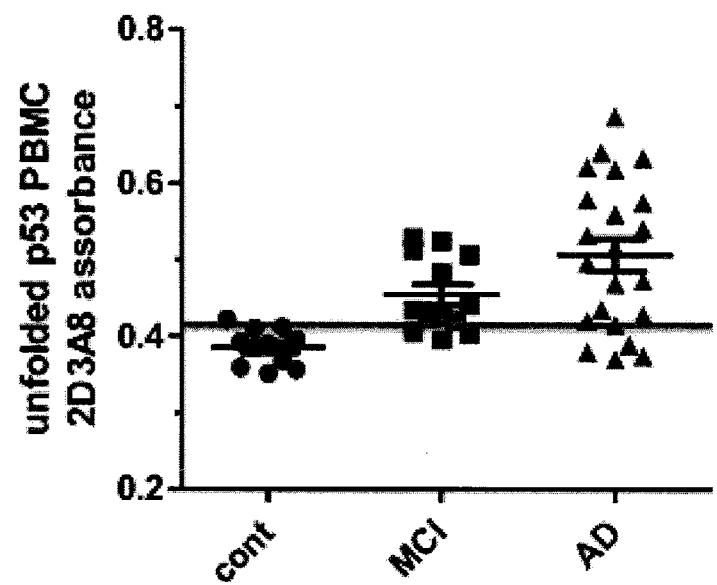
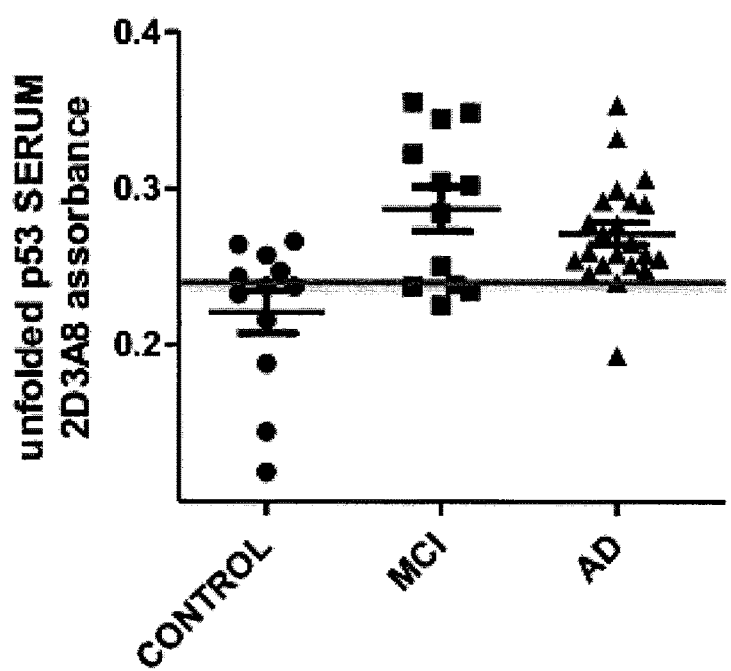

SEQUENCE LISTING

```
<160> NUMBER OF SEQ ID NOS: 3

<210> SEQ ID NO 1
<211> LENGTH: 16
<212> TYPE: PRT
<213> ORGANISM: Homo sapiens

<400> SEQUENCE: 1

Arg Arg Thr Glu Glu Glu Asn Leu Arg Lys Lys Gly Glu Pro His His
1               5                   10                  15

<210> SEQ ID NO 2
<211> LENGTH: 16
<212> TYPE: PRT
<213> ORGANISM: Homo sapiens

<400> SEQUENCE: 2

Cys Arg Thr Glu Glu Glu Asn Leu Arg Lys Lys Gly Glu Pro His His
1               5                   10                  15

<210> SEQ ID NO 3
<211> LENGTH: 392
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Ala
145                 150                 155                 160

Ile Tyr Lys Gln Ser Gln His Met Thr Glu Val Val Arg Arg Cys Pro
                165                 170                 175

His His Glu Arg Cys Ser Asp Ser Asp Gly Leu Ala Pro Pro Gln His
            180                 185                 190

Leu Ile Arg Val Glu Gly Asn Leu Arg Val Glu Tyr Leu Asp Asp Arg
        195                 200                 205
```

-continued

```
Asn Thr Phe Arg His Ser Val Val Pro Tyr Glu Pro Pro Glu Val
    210             215             220
Gly Ser Asp Cys Thr Thr Ile His Tyr Asn Tyr Met Cys Asn Ser Ser
225             230              235             240
Cys Met Gly Met Asn Arg Arg Pro Ile Leu Thr Ile Ile Thr Leu
            245             250             255
Glu Asp Ser Ser Gly Asn Leu Leu Gly Arg Asn Ser Phe Glu Val Arg
            260             265             270
Val Cys Ala Cys Pro Gly Arg Asp Arg Arg Thr Glu Glu Glu Asn Leu
            275             280             285
Arg Lys Lys Gly Glu Pro His His Glu Leu Pro Pro Gly Ser Thr Lys
    290             295             300
Arg Ala Leu Pro Asn Asn Thr Ser Ser Ser Pro Gln Pro Lys Lys Lys
305             310             315             320
Pro Leu Asp Gly Glu Tyr Phe Thr Leu Gln Ile Arg Gly Arg Glu Arg
            325             330             335
Phe Glu Met Phe Arg Glu Leu Asn Glu Ala Leu Glu Leu Lys Asp Ala
            340             345             350
Gln Ala Gly Lys Glu Pro Gly Gly Ser Arg Ala His Ser Ser His Leu
            355             360             365
Lys Ser Lys Lys Gly Gln Ser Thr Ser Arg His Lys Lys Leu Met Phe
    370             375             380
Lys Thr Glu Gly Pro Asp Ser Asp
385             390
```

ANTIBODY BINDING A LINEAR EPITOPE OF HUMAN P53 AND DIAGNOSTIC APPLICATIONS THEREOF

BACKGROUND OF THE INVENTION

The present invention lies in the field of immunodiagnostics.

More particularly, the present invention relates to an antibody, a kit and in vitro methods of diagnosing Alzheimer's disease and/or the predisposition of a subject to develop Alzheimer's disease or cognitive impairment during ageing.

The DNA binding domain (DBD) of human p53 protein (aa 101-306) is characterized by high-grade conformational flexibility and contains one $Zn^{2+}$ ion coordinated by three cysteines (residues 176, 238 and 242) and one histidine (residue 179). In the wild-type isoform of human p53 protein, the aa 282-297 linear epitope is masked and therefore not available for recognition by an epitope-specific antibody.

However, because of the high-grade flexibility of its DBD domain, p53 protein can assume several conformations, which also characterize its biological activity.

In its wild-type conformation, p53 can bind DNA consensus sequences and transcribe/repress the expression of target genes. In this conformation, the protein exposes an epitope which is recognized by the commercially available, conformationally specific antibody named PAb1620.

There are several grades of conformational alteration states of p53, which correspond to different conformationally altered isoforms. Some mutations in the p53 gene cause a conformational change of the protein, which corresponds to a conformationally altered isoform capable of being recognized by commercially available, conformationally specific antibodies.

Additional conformationally altered isoforms may also derive from post-translational modifications, such as oxidation and/or nitration reactions, which alter the wild-type tertiary structure of the protein.

Buizza L. et al. ("Conformational altered p53 as an early marker of oxidative stress in Alzheimer's disease", PlosOne 7(1):e29789) and Uberti D et al. ("Identification of a mutant-like conformation of p53 in fibroblasts from sporadic Alzheimer's disease patients", Neurobiology of Aging 27 (2006) 1193-1201) both identify the expression of mutated p53 protein in patients with Alzheimer's disease, such identification having been made using the anti-p53 antibody PAb240 which binds a cryptic epitope on the amino acid residues 213-217 of p53 protein, not detectable in the wild-type p53 protein.

BRIEF SUMMARY OF THE INVENTION

The present inventors have unexpectedly found an anti-human p53 which has proved capable of specifically and selectively recognize a conformationally altered isoform of the protein resulting from its post-translational modifications, in which the aa 282-297 linear epitope is exposed.

The inventors have also unexpectedly observed that the isoform of p53 protein recognized by the antibody of the invention is peculiarly expressed in subjects with Alzheimer's disease. In particular, the conformationally altered isoform recognized by the antibody of the invention is expressed in higher amounts in biological samples—particularly in samples of blood cells, neuronal cells or other cell types, as well as in samples of biological fluids such as, for example, blood, plasma, serum, saliva, urine—of patients with Alzheimer's disease.

The inventors further observed that such conformationally altered isoform recognized by the antibody of the invention is also expressed in biological samples of subjects with Mild Cognitive Impairment (MCI).

Therefore, the antibody of the invention is a useful diagnostic and prognostic tool, for diagnosing Alzheimer's disease and for determining the predisposition of a subject with Mild Cognitive Impairment (MCI) to develop Alzheimer's disease.

Finally, the inventors observed that the expression of the p53 protein isoform positive to the antibody of the invention in a statistically significant manner correlates with the age and cognitive impairment of the subjects studied.

Therefore, the antibody of the invention is also useful for determining the predisposition of a subject to develop cognitive impairment during ageing.

BRIEF DESCRIPTION OF THE DRAWINGS

FIG. 1 discloses a P53 protein sequence;

FIG. 3 discloses experimental data of example 4 of unfolded P53 PBMC 2d3A8 absorbance versus CONT, MCI and AD;

DETAILED DESCRIPTION OF THE INVENTION

Figure 2:
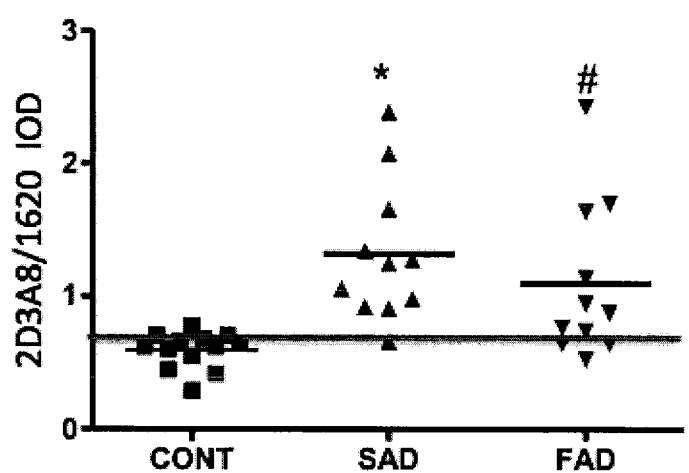
FIG. 2 discloses experimental data of 2d3A8/1620 ration versus CONT, SAD and FAD.

A first object of the present invention is therefore an anti-human p53 antibody, characterized in that it recognizes the linear epitope of sequence RRTEEENLRKKGEPHH (SEQ ID NO:1) present in the DNA binding domain (DBD) of human p53, said linear epitope spanning between the amino acid positions 282-297 of the amino acid sequence of human p53.

The preparation of the antibody of the invention is described in the following experimental part.

In a preferred embodiment, the antibody of the invention is a monoclonal antibody.

The antibody of the present invention can be obtained by any well-known methodology for the preparation of polyclonal or monoclonal antibodies. In the following experimental part, the preparation of the antibody by animal (mice) immunization with an antigen consisting of a peptide of sequence CRTEEENLRKKGEPHH (SEQ ID NO:2) conjugated with bovine serum albumin as carrier and hybridoma technique is described by way of example.

As previously mentioned, the antibody object of the present invention specifically recognizes an isoform of human p53 protein which has been shown to be correlated to Alzheimer's disease and development of cognitive impairment during ageing. Such antibody therefore represents a useful diagnostic and prognostic tool.

An in vitro method of determining an isoform conformationally altered by post-translational modification of p53 protein peculiar of Alzheimer's disease, as well as the diagnostic and prognostic methods as defined in the appended claims which form an integral part of the present description, are also part of the present invention.

The method detects the formation of an immunocomplex between the human p53 protein and the antibody in the sample.

An immunodiagnostic kit as defined in the appended claims is also part of the present invention.

In order to implement the methods and kit of the invention any type of well-known immunoassay can be used, such as for example immunoprecipitation assay, ELISA or RIA, immunofluorescence, Western Blot, FACS analysis, immunocytochemistry/immunohistochemistry. An immunoassay kit may include the antibody and means for detecting the binding of the antibody to human p53 protein.

The following non-limitative examples are provided to illustrate the scope of the invention as defined by the appended claims.

Example 1

1a. Immunization

For the immunization, 6/8 week old mice which were healthy and disorder-free were used. The peptide used as antigen for antibody production had the following features:
Sequence: "N-terminal" CRTEEENLRKKGEPHH "C terminal" (SEQ ID NO: 2)
Length: 16 amino acids
Molecular weight: 1960.94
Purity: 96.4%
Form: lyophilized powder
Conjugation: Conjugated with BSA by the glutaraldehyde method The p53 protein sequence (SEQ ID NO: 3) is depicted in FIG. 1, where the DNA binding domain (DBD) is highlighted in grey, the linear epitope recognized by 2D3A8 antibody is underlined.

The first injection has been performed by emulsifying the antigen (50 µg) in Freund's complete adjuvant (FCA). The subcutaneous injections have been performed in 2-3 sites on the animal. Additional injections have been performed at 3-week intervals with 50 µg of antigen emulsified in Freund's incomplete adjuvant (FIA). The antibody titer is evaluated by ELISA.

In the ELISA assay, the antibody titer present in the serum of 5 mice was evaluated after the third injection with the above-described peptide. The blood of immunized mice was collected from their caudal veins. The absorbance values obtained following the spectrophotometric reading provided important information on the antibody titer present in the various mice. Animals were subjected to further additional injections so that the antibody titer reached a sufficiently high level. The mouse with the best antibody titer was chosen for the first fusion.

1b. Development of Hybridomas

The animals' splenocytes were fused with mouse myeloma cells (SP2/O cell line). The fusion products were subjected to screening against the antigen to select the antibody-producing clones. The growth of these clones was continued. This first screening was performed by ELISA methodology. The positive clones were labeled as "parental clones" and frozen after 3 passages. An antigen coating was created onto ELISA plates, and successively the fusion product supernatant was added. The serum of the immunized animals was used as a positive control in ELISA (Example 2).

Example 2

After the fusion between the splenocytes of the mouse with the best antibody titer and mouse myeloma cells, an ELISA assay was performed to evaluate the fusion products. A coating with the antigen was created in a 96-well ELISA plate and serial dilutions of the supernatant from various clones were added to each well to evaluate their antibody production by spectrophotometric reading. The clones with the highest optical density at 450 nm ($OD_{450nm}$) were transferred to 24-well plates and after their growth the ELISA assay was repeated, the clones with the highest antibody production were transferred to 6-well plates, grown and tested again by ELISA. The procedure was repeated also for the clones transferred to culture flasks. These successive assays allowed the identification of the best clones which were tested for the last time by ELISA, with the limit dilution method to ensure that the positive clones showed an actual antibody response.

The validated antibody was purified from the supernatant of the clone with the highest $OD_{450nm}$ value and therefore with the best antibody titer. This antibody is named "clone 2D3A8" for brevity.

Example 3

Study of the expression of the conformationally altered isoform of p53 protein recognized by 2D3A8 antibody in patients with sporadic and familial Alzheimer's disease and MCI.

In immortalized B lymphocytes of patients diagnosed with sporadic Alzheimer (SAD) and familial Alzheimer (FAD), the conformational state of p53 was evaluated by the immunoprecipitation method, using two conformationally specific antibodies which recognize the wild-type isoform of the protein (PAb 1620) and a conformationally altered isoform (2D3A8). The immunoprecipitate was then visualized by Western Blot with a polyclonal anti-p53 antibody (CM1). The experimental data were expressed as ratio between the intensity of the band positive to 2D3A8 antibody and to PAb1620 of the same sample.

In SAD and FAD samples, the 2D3A8/1620 ratio was significantly higher compared to the lymphocytes of dementia-free control patients (FIG. 2).

2D3A8 antibody can therefore discriminate a conformationally altered isoform of p53 peculiarly expressed in immortalized lymphocytes of patients with sporadic (SAD) and familial (FAD) Alzheimer.

Example 4

In samples of fresh blood of patients diagnosed Alzheimer and of subjects with mild cognitive impairment, diagnosed MCI, the conformationally altered isoform of p53 recognized by 2D3A8 antibody (2D3A8-positive p53) was evaluated by ELISA. Healthy, dementia-free subjects of the same age were also evaluated.

2D3A8-positive p53 vas detected both in blood cells (PBMC) and in serum of the same patients or subjects. 2D3A8 antibody can recognize with high-specificity grade patients with Alzheimer. Interestingly, subjects with mild cognitive impairment express serum levels of 2D3A8-positive p53 statistically higher than the levels of protein isoform present in control subjects. In PBMCs and in serum of patients with Alzheimer, the 2D3A8-positive p53 isoform was statistically increased compared to the controls (FIG. 3).

Example 5

The 2D3A8-positive p53 isoform correlates with age.

Figure 4:
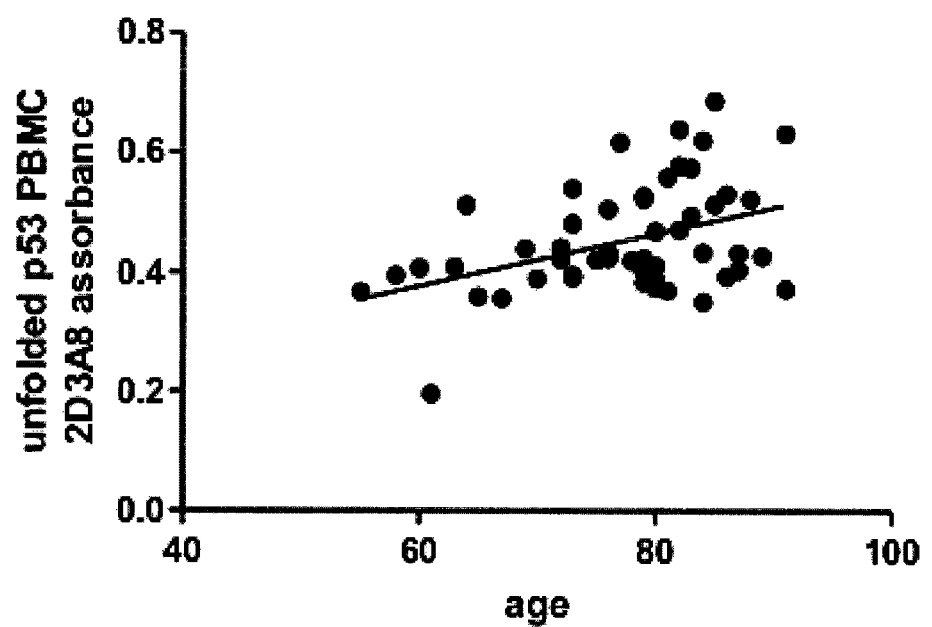
FIG. 4 discloses experimental data of example 5, during ageing, of unfolded P53 PBMC 2d3A8 absorbance versus CONT, MCI and AD.

During ageing, the expression of 2D3A8-positive p53 in blood cells (PBMC) increases in a statistically significant manner (FIG. 4).

Figure 5:
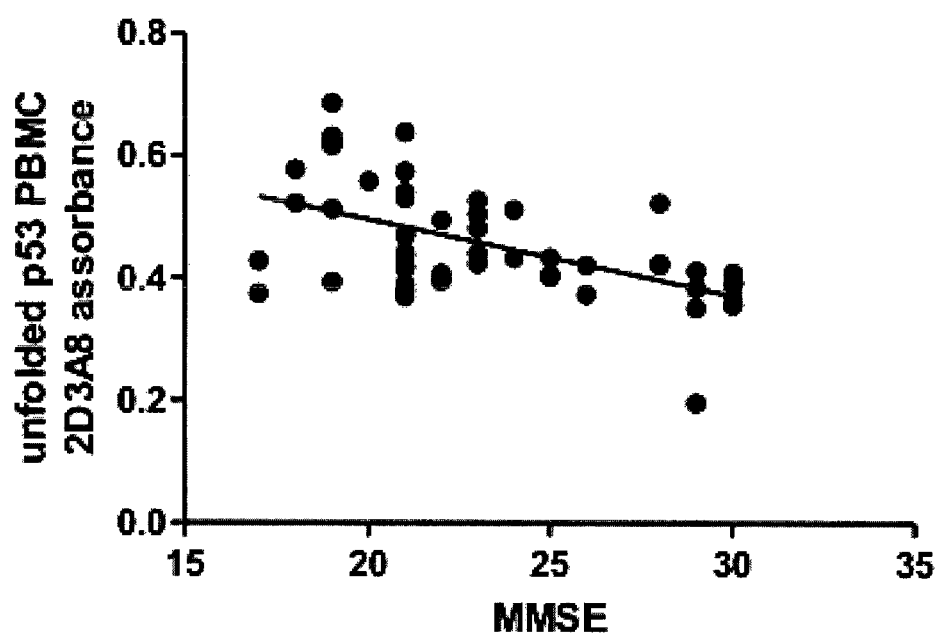
FIG. 5 discloses experimental data of example 5, decreasing of the scoring in the MMSE test, of unfolded P53 PBMC 2d3A8 absorbance versus CONT, MCI, and AD.

Moreover, the expression of 2D3A8-positive p53 correlates with the cognitive status, measured by the well-known neuropsychological test MMSE. The 2D3A8-positive p53 isoform increases with the decrease of the scoring obtained in the MMSE test, i.e., it increases with the progression of cognitive impairment (FIG. 5).

---

The invention claimed is:

1. A method of preparing an anti-human p53 antibody comprising the steps of: (i) immunizing an animal with an immunogen comprising a peptide of the human p53 protein of sequence CRTEEENLRKKGEPHH (SEQ ID NO: 2) conjugated with a carrier; and (ii) isolating the antibody obtained upon immunization, wherein it binds to the linear epitope of human p53 of sequence RRTEEENLRKKGEPHH (SEQ ID NO: 1).

2. The method of preparing an antibody according to claim 1, wherein the carrier is bovine serum albumin.

* * * * *